United States Patent
Treacy et al.

(10) Patent No.: US 9,852,265 B1
(45) Date of Patent: Dec. 26, 2017

(54) SYSTEM AND METHOD OF MEDICAL DEVICE ALARM MANAGEMENT

(71) Applicant: General Electric Company, Schenectady, NY (US)

(72) Inventors: Stephen Thomas Treacy, Milwaukee, WI (US); Marriaine Sien Hak, Arlington, VA (US); Mary Jane Stover, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/281,717

(22) Filed: Sep. 30, 2016

(51) Int. Cl.
*G06F 19/00* (2011.01)
*G08B 5/22* (2006.01)

(52) U.S. Cl.
CPC ........ *G06F 19/3418* (2013.01); *G06F 19/322* (2013.01); *G08B 5/222* (2013.01)

(58) Field of Classification Search
CPC ............. G06F 19/3412; G06F 19/3418; G06F 19/3406; G06F 3/04842; G06F 19/322; A61B 5/746; G08B 29/02; G08B 5/222
See application file for complete search history.

(56) References Cited

U.S. PATENT DOCUMENTS

2017/0098358 A1* 4/2017 Bechtel ............... G06F 3/04842

* cited by examiner

*Primary Examiner* — Curtis Odom
(74) *Attorney, Agent, or Firm* — Andrus Intellectual Property Law, LLP (57) ABSTRACT

Systems and methods of medical device alarm management include receiving alarm data from a plurality of medical devices. The alarm data includes a plurality of alarms from the plurality of medical devices. A summary of the received alarms from the plurality of medical devices is visually presented. Upon receiving a selection of a medical device of the plurality of medical devices, an identification of each of the alarms from the selected medical device is visually presented. A frequency of each of the alarms from the selected medical device is visually presented.

22 Claims, 9 Drawing Sheets

SYSTEM AND METHOD OF MEDICAL DEVICE ALARM MANAGEMENT

BACKGROUND

The present disclosure relates to the field of medical devices. More specifically, the present disclosure relates to systems and methods for management of medical device alarms.

In a hospital setting, care units use a variety of medical devices to monitor the patient and/or to provide therapy to patients. In the course of operation, these devices generate alarm events which range from routine to critical in the specific severity of each of the events that the alarms are indicating.

Automated alarms can be beneficial to algorithmically determine when an event related to a patient monitoring or patient therapy device has occurred. These algorithms generally compare one or more parameters from the medical device to one or more predefined threshold settings. Alarms algorithms may be threshold comparisons, but may also include logical combinations and using Boolean and/or fuzzy logic. These automated alarms can be beneficial to draw clinician attention to the detection and/or occurrence of an event.

While each alarm indicates a condition or event of some importance or relevance, a significant number of alarms can be generated during routine care and these alarms place a burden both on patients who may be bothered (e.g. woken up) or concerned by alarm events as well as on clinicians who must divert time and attention from other care, tasks, or activities to attend to alarms. A significant number of clinically irrelevant alarms can create alarm fatigue in clinicians whereby the attention to the large volume of alarms can slow recognition or response to alarms indicating less frequent but more importance or critical events.

Therefore, systems and methods that enable the investigation of alarm event causes and management of alarms can help clinicians to investigate, propose and evaluate solutions to, and implement efforts to reduce alarm burden on clinicians.

BRIEF DISCLOSURE

An exemplary embodiment of a system for medical device alarm management includes a plurality of medical devices. The plurality of medical devices produce medical device data and generate a plurality of alarms based upon analysis of the medical device data. A processor receives alarm data identifying each of the plurality of alarms from each of the plurality of medical devices. The processor receives the medical device data from the plurality of medical devices. The processor categorizes each of the plurality of alarms in the alarm data and aggregates the alarm data. A graphical display is operable by the processor to visually present a summary of the plurality of alarms identified in the received alarm data. The summary includes a total of the plurality of alarms, each medical device's contribution to the total of the plurality of alarms, and a category of each of the plurality of alarms. A user input device is communicatively connected to the processor and operable to receive at least one user input. The at least one user input includes a selection of a medical device of the plurality of medical devices. Upon receiving the selection of the medical device, the processor operates the graphical display to visually present an identification of each of the alarms from the selected medical device and a frequency of each of the alarms from the selected medical device.

An exemplary embodiment of a method of medical device alarm management includes receiving alarm data from a plurality of medical devices. The alarm data includes a plurality of alarms from the plurality of medical devices. A summary of the received alarms from the plurality of medical devices is visually presented. Upon receiving a selection of a medical device of the plurality of medical devices, an identification of each of the alarms from the selected medical device is visually presented. A frequency of each of the alarms from the selected medical device is visually presented.

An exemplary embodiment of a method of medical device alarm management includes receiving alarm data from a plurality of medical devices. The alarm data includes a plurality of alarms from the plurality of medical devices. Medical device data is received from the plurality of medical devices. The medical device data having been processed by a respective medical device of the plurality of medical devices using at least one alarm parameter to initiate the plurality of alarms in the alarm data. A summary of alarms received in the alarm data from the plurality of medical devices is visually presented. A total alarm burden from a total number of alarms from each of the plurality of medical devices is aggregated. Each medical device's contribution to the total alarm burden is calculated. Each medical device's contribution to the total alarm burden is visually presented. Upon receiving a selection of a medical device of the plurality of medical devices, an identification of each of the alarms from the selected medical device is visually presented. A frequency of each of the alarms from the selected medical device is visually presented.

DETAILED DISCLOSURE

Medical device alarms are helpful to draw clinician attention to automatedly detected events. However, if too many clinically irrelevant alarms are initiated too frequently, this can distract clinicians and bother patients. Therefore, interventions are often needed to tailor the practices and alarms to the conditions in which the medical devices are used. For example, different patient care units within a hospital may experience different frequencies of particular alarms and individual patients may be more prone to alarms, for example if a patient's baseline or median measurement of a particular parameter approaches a value of an alarms threshold.

However, identifying and implementing interventions to address alarm burden require monitoring, visualization, and analysis tools in order to assist clinicians and/or clinical managers in making and implementing such decisions. The systems and methods as disclosed herein provide these such tools to clinicians and/or clinical managers.

Figure 1:
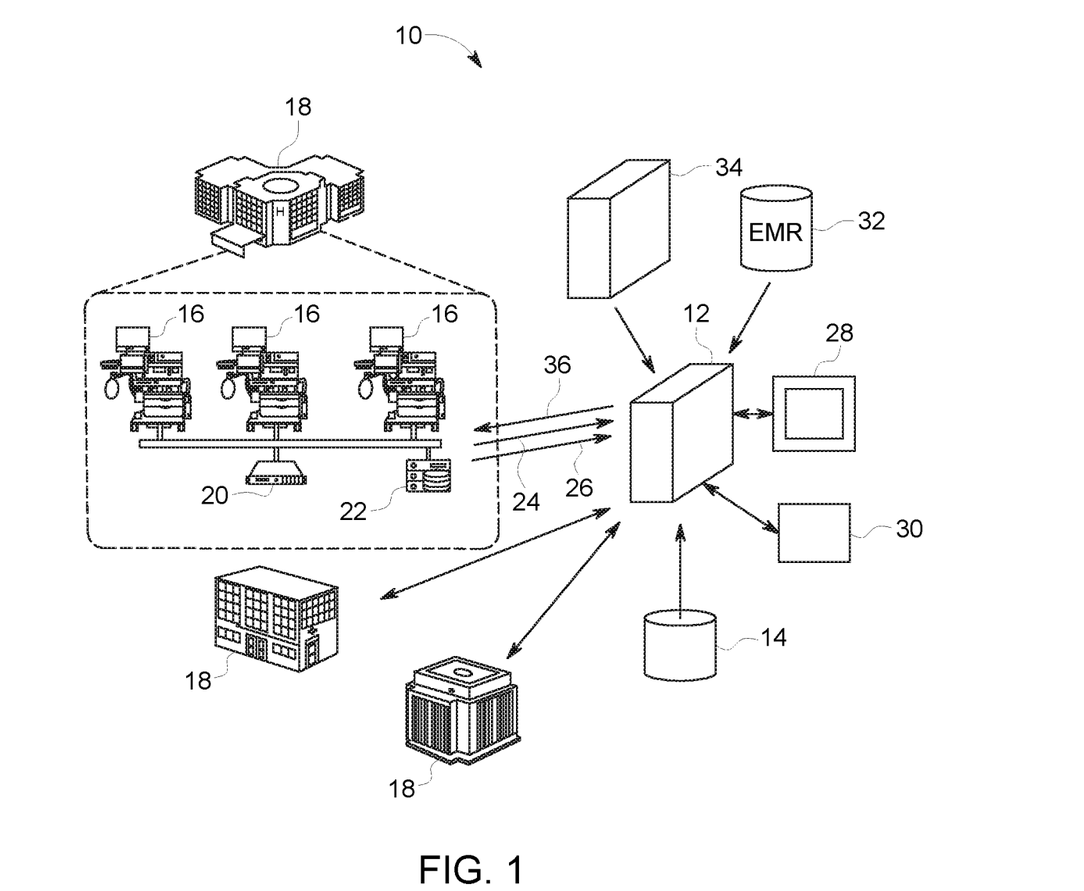
FIG. 1 depicts an exemplary embodiment of a system for medical device alarm management.

FIG. 1 depicts an exemplary embodiment of a medical device alarm management system. The system 10 exemplarily includes a processing unit 12. The processing unit 12 is communicatively connected to a computer readable medium 14 upon which data, algorithms, and computer programs embodied in computer readable code are stored for access by the processing unit 12. The processing unit 12 accesses and executes such algorithms and/or computer programs to carry out the functionality as described in further detail herein. In an exemplary embodiment, the computer readable medium 14 may exemplarily be an integral part of the processing unit or may be located remote from the processing unit 12 and be communicatively connected thereto.

The processing unit 12 exemplarily includes a microprocessor or microcontroller and in embodiments may be a specific use controller or a general purpose computer. The processing unit 12 is exemplarily communicatively connected to a plurality of medical devices 16 located at one or more hospitals 18. Thus, in examples, the processing unit 12 may be communicatively connected to a plurality of hospitals 18 or other medical facilities with medical devices at a plurality of locations, for example across a hospital or provider network. Furthermore, within a hospital 18, the medical devices 16 may be located in a plurality of medical care units. Each medical care unit may be specific to a particular type of care. Non-limiting examples of medical care units include, but are not limited to emergency rooms (ER), intensive care units (ICU), specialty intensive care units, for example cardiovascular ICU (CVICU), neonatal ICU (NICU), pediatric ICU (PICU), coronary care units (CCU), post op day one units (POD1) or post op day 2 units (POD2).

The medical devices 16 are exemplarily communicatively connected by a local network which may be operated by a local server 20 which may exemplarily handle and process the data from each of the medical devices 16 in a hospital or medical care unit. In an exemplary embodiment, wherein the system 10 is implemented at a single hospital or other location, the processing unit 12 may communicate with the local server 20. In a more distributed or cloud based implementation, a communications gateway 22 may communicatively connect the local server 20 to the processing unit 12. The processing unit 12 exemplarily receives alarm data 24 and medical device data 26 for each of the medical devices 16 exemplarily through at least one of the local server 20 and the communications gateway 22. As will be described in further detail herein, the processing unit 12 processes the alarm data 24 and medical device data and visually presents results of this processing on a graphical display 28 which is communicatively connected to and operable by the processing unit 12.

At least one user input device 30 is similarly communicatively connected to the processing unit 12 and receives user inputs in response to the visual presentations on the graphical display 28 and further carries out exemplary embodiments of the method as disclosed in further detail herein. The user input device 30 may exemplarily include, but is not limited to a keyboard, a mouse, or a touch screen input capability of the graphical display 28. Embodiments of the system 10 further communicatively connect the processing unit 12 to other sources of patient data, for example patent electronic medical records 32 exemplarily stored in one or more databases at one or more computer readable media. The processing unit 12 may further be communicatively connected to a personnel management unit 34 which may be embodied in a separate computer processor or processors or other computer systems and in exemplary embodiments may provide staffing or personnel information to be incorporated into analysis of medical device alarms as disclosed in further detail herein. In other embodiments, the graphical display 28 may be remotely located for a user in a different location than the medical device, or in other embodiments, the graphical display may be located in conjunction with the medical device, or a central care unit monitor (not depicted) to which a plurality of medical devices 16 may be communicatively connected.

In some embodiments as described in further detail herein the processing unit 12 is used to facilitate clinician proposal, evaluation, and selection of updates to alarm value limits of automated alarms. These and other alarm settings 36 may be communicated back to one or more medical devices from the processing unit 12 for implementation at one or more medical devices 16 individually, across medical devices in a medical care unit, across medical devices within a hospital 18, or across an entire provider network.

Figure 2:
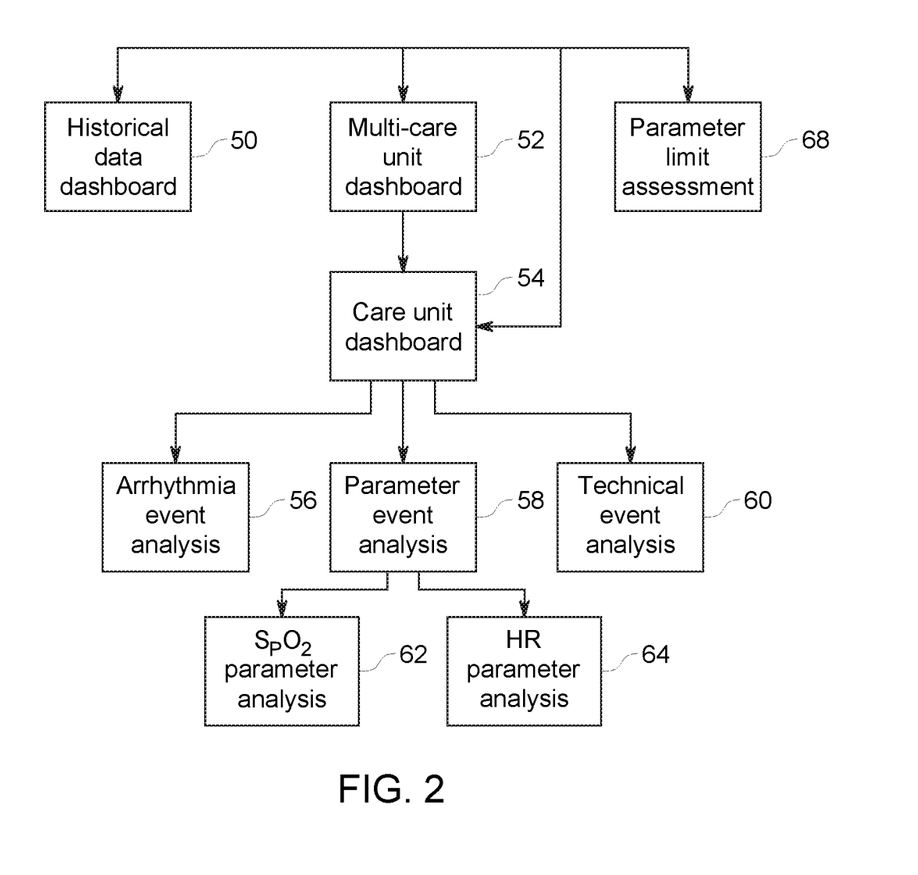
FIG. 2 is an exemplary navigation map of graphical user interfaces.

FIG. 2 is an exemplary and non-limiting embodiment of a navigation map of various visual representations and graphical user interfaces (GUI) as may be produced and used as described in further detail herein in carrying out exemplary embodiments of the systems and methods of medical device alarm management.

Figure 4:
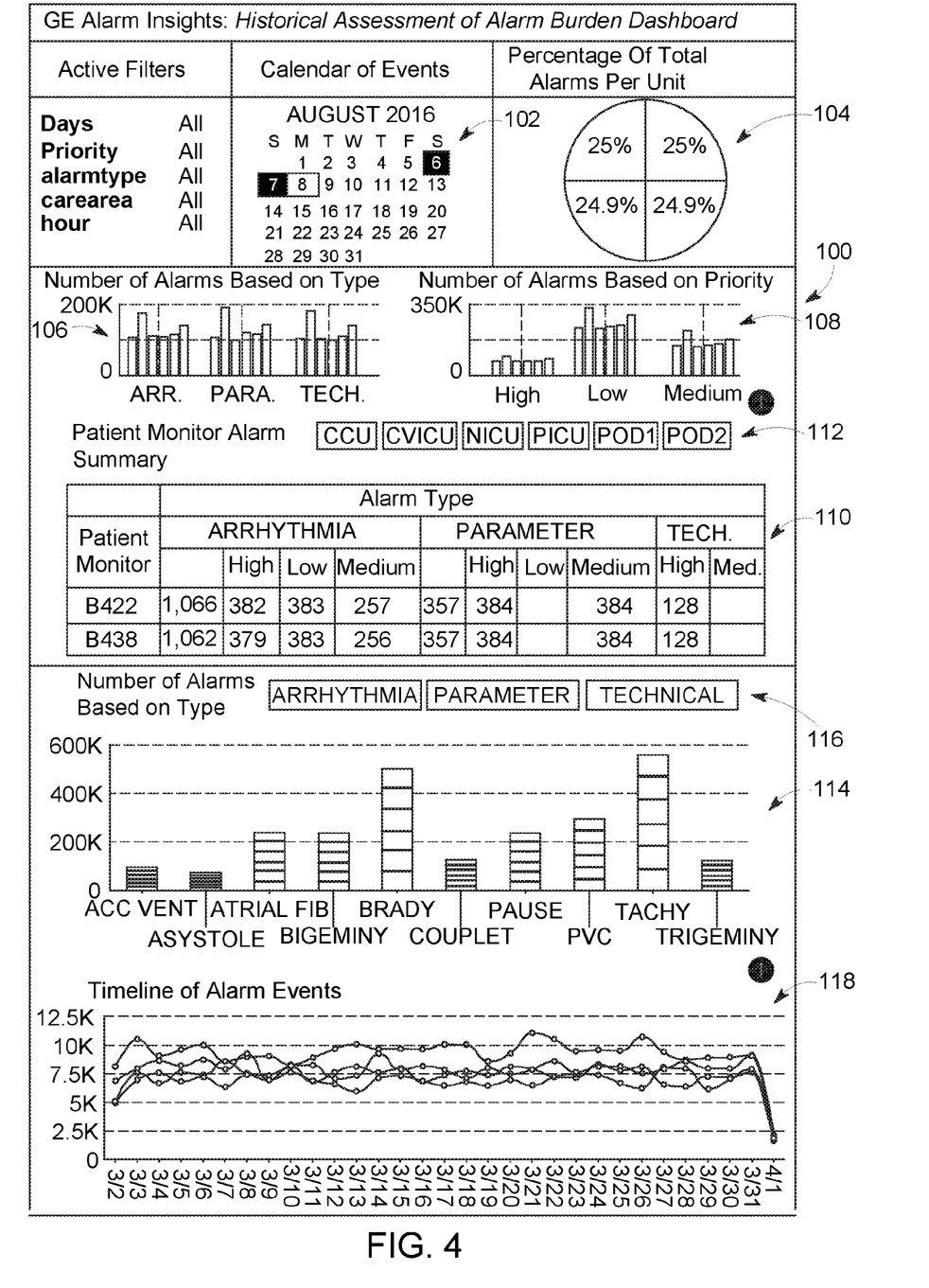
FIG. 4 depicts an exemplary embodiment of a historical data dashboard graphical user interface.

A historical data dashboard 50 is exemplarily depicted in the historical dashboard GUI 100 in FIG. 4. As depicted in FIG. 4, a calendar 102 is available for a user to select the temporal duration of the historical data to be presented. In an exemplary embodiment, the user has an option to select any particular day or to present a summary of the alarms received over a month or another length of time. At 104, a graphical depiction of the alarm burden contribution from each of the monitored locations or units is presented. In an exemplary embodiment, this is presented as one or both of a visual graph and a numerical value (e.g. a percentage). In another embodiment, the total numbers of alarms from each unit may be presented instead of or in addition to a percentage of that care unit's contribution to the total alarm burden. The alarm burden is further visually presented with graph 106 that presents the total number of alarms in the selected time range broken down by location of the alarm (e.g. CCU, CVICU, NICU, PICU, POD1, OR POD2) and by alarm type (e.g. arrhythmia alarms, parameter alarms, or technical alarms). Graph 108 presents the alarm totals based upon alarm location and alarm priority. Different specific alarms in each of the exemplary alarm types of arrhythmia alarms, parameter alarms, and technical alarms may further have a priority associated with the initiation of such alarm. In an example, different threshold values for the same alarm may define alarms with different priorities. Additionally, some alarms may have a high priority if such alarm is indicative or associated with a critical patient condition for example tachycardia or ventricular fibrillation while other alarms may have a low priority if the alarm is more routine or not associated with negative patient outcomes, for example completion of an IV infusion.

In an exemplary embodiment, arrhythmia alarms may include, but are not limited to: accelerated ventricular, ventricular asystole, atrial fibrillation, bigeminy, bradycardia, couplets, QRS pause, premature ventricular complexes (PVC), tachycardia, and trigeminy alarms. In an exemplary embodiment, parameter alarms may include, but are not limited to: detection of apnea, high arterial mean pressure, high arterial systolic pressure, low arterial systolic pressure, high heart rate, low heart rate, high respiratory rate, low respiratory rate, high blood oxygenation ($S_PO_2$) and low $S_PO_2$. In an exemplary embodiment, technical alarms may include, but are not limited to: arrhythmia pause, arrhythmia suspend, change battery, check NIBP, loose blood pressure cuff, IP removed, no $S_PO_2$ probe, Noisy ECG, off network, or sensor failure.

At 110 a table provides a clinician with access to device specific alarm totals from the selected time period. Navigation buttons 112 may be selected by the user to refine the table 110 to the devices in a particular monitored location or unit of the facility.

At 114 a visual presentation of a summary of specific alarms that contributed to overall alarm burden are presented. For example, a clinician can select a navigation button 116 to select a particular type of alarm, for example arrhythmia alarms and the graphs 114 shows the total number of each of the alarms of the arrhythmia type that occurred at each of the monitored locations.

At 116 a visual presentation of daily historical number of alarm events is presented. Exemplarily, the daily alarm event totals are presented on a location basis although it will be recognized that in other embodiments, the alarm totals may be presented based upon alarm type or alarm priority. Such a visual presentation of alarm burden can exemplarily help to identify hospital units or locations which have more or fewer alarms or more or fewer alarm types. Investigation of these areas can help to direct clinician efforts for example with the tools as described in further detail herein, to address clinical alarm burden and manage alarms.

Embodiments of the historical data dashboard GUI 100 visually present alarm burden over a selected time period to a reviewing clinician or technician. By user interactions and inputs into this GUI, the user can explore and gain insight into contributing factors to alarm burden in a particular unit, from a population of beds/patients, alarm burden for a particular patient, or to specific alarm events.

In an exemplary embodiment, a reviewing clinician may use the historical dashboard GUI 100 and exemplarily the historical number of alarm events at 116 to evaluate changes implemented to reduce alarm burden. For example, a clinician may decide upon and implement a change to one or more alarm setting parameters in the manners as described in further detail herein and after making note of when such changes were implemented can evaluate the historical alarm record as presented on a daily basis to determine if such changes have an identifiable impact on alarm burden. When alarm burden is presented in a comparison between care units, changes implemented in one care unit can be compared against another and/or a comparable care unit to evaluate proposed changes before implementing such changes to other care units.

Referring back to FIG. 2, the clinician or technician may navigate to a multiple care unit dashboard at 52. An exemplary embodiment of a multiple care unit dashboard GUI 120 is presented at FIG. 5. In an exemplary embodiment, the multiple care unit dashboard presents real time or near real time information regarding alarm burden across multiple care units. While the historical data dashboard GUI presented alarm burden data encompassing days or months of alarms and available to data from historical data set. A time interval input 122 exemplarily receives a selection of a time interval from the present or most recently available data extending backwards a selected number of hours. As a non-limiting example, time intervals of 4 hours, 8 hours, 12 hours, or 24 hours are available for selection by the user. It will be recognized that these time intervals are merely exemplary and that in alternative embodiments the user may input a custom number of hours or time frame and that such selected time frame may be shorter (including time intervals less than an hours) or longer than depicted including, but not limited to 48 hours or 72 hours. A highlighted selection 124 visually indicates to the user the current selected time interval for alarm burden data. Upon selecting the time interval, the GUI 120 may refresh with the currently available alarm burden data. A time range indication 126 specifies to the user the time of the most recently acquired alarm data and the start time associated with the presented data according to the selected time interval. In an exemplary embodiment, a user may select a refresh button 128 to update the presentation with newly received alarm data. The time range indication 126 would update accordingly to reflect the time of the most recently received data and recalculate the start time of the data according to the selected time interval.

Figure 5:
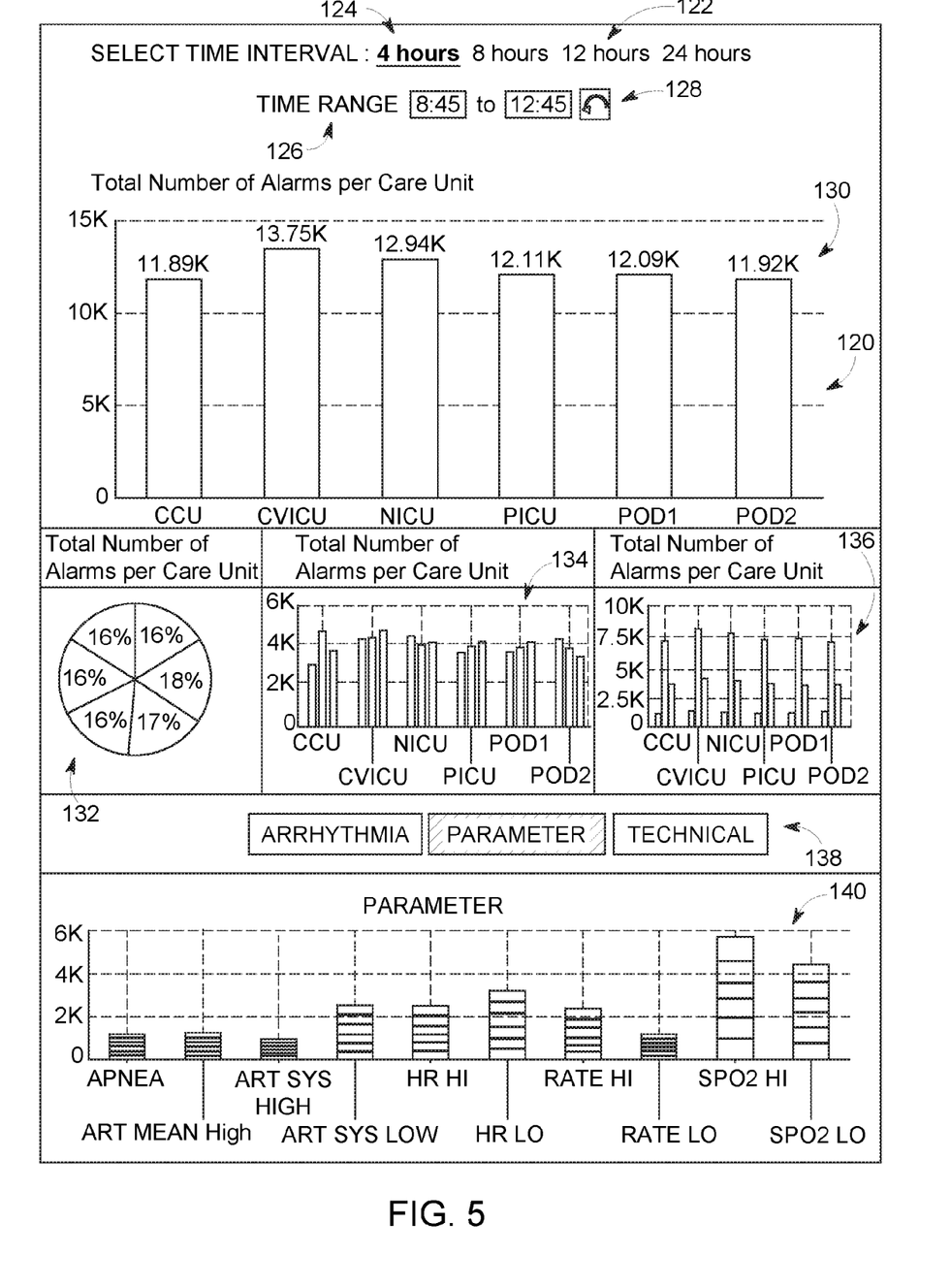
FIG. 5 depicts an exemplary embodiment of an alarm burden dashboard graphical user interface.

The GUI 120 visually presents a summary of the current alarm burden at each of a plurality of care units. A graph 130 present the current total numbers of alarms at each of the monitored care units during the most recent selected time interval. The graph 132 presents this same information as a percentage of the total number of alarms in the medical care facility broken down by percentage contribution of the total number by each of the care units. Graph 134 exemplarily breaks down the total number of alarms per unit into the constituent types of alarms for example, arrhythmia alarms, parameter alarms, and technical alarms. Graph 136 visually presents the break down of priority of current alarms by each care unit. The user is able to select an input button 138 to select between alarm types or in a further embodiment between alarm priorities and the system produces a graph 140 that visually presents a breakdown of the numbers of alarms experienced at each of the care units by the specific alarm within a selected alarm type. For example, the parameter alarm type is selected in the navigation buttons 138 and the graph 140 presents the total numbers of current alarms in each of the care units for a specific monitored parameter alarms.

Embodiments of the multiple care unit alarm burden dashboard GUI 120 visually present a summary of current alarm burden across multiple care units to a clinician. As will be described in further detail herein, embodiments enable clinicians to navigate through alarm burden data to assess causes and factors in current alarm burden and to propose, test, accept, and implement changes to alarm settings to alleviate alarm burden. In an exemplary embodiment, the user may select any of the specific graphs associated with a care unit as presented in any of the graphs in GUI 20, for example, graphs 130, 132, 134, 136, or 140 to navigate a care unit alarm burden dashboard represented at 54 in FIG. 2 or as exemplarily shown in greater detail as GUI 142 in FIG. 6. Alternatively, a user may navigate directly to a specific care unit alarm burden dashboard 54 without navigating through the multiple care unit alarm burden dashboard GUI 120.

The care unit alarm burden dashboard GUI 142 exemplarily presents current alarm burden data for a time interval selected at 144 or a particular care unit of a plurality of care units monitored by the system. As exemplarily shown in FIG. 6, the care unit alarm burden dashboard GUI 142 presents alarm data for the CVICU hospital unit. The time range is for the current data is presented at 146 based upon the user selection at 144 and a time of the most recently received alarm data. The user can further select filters 148 to further refine the presented current alarm data, exemplarily to refine the presentation by alarm priority and/or by alarm type.

Figure 6:
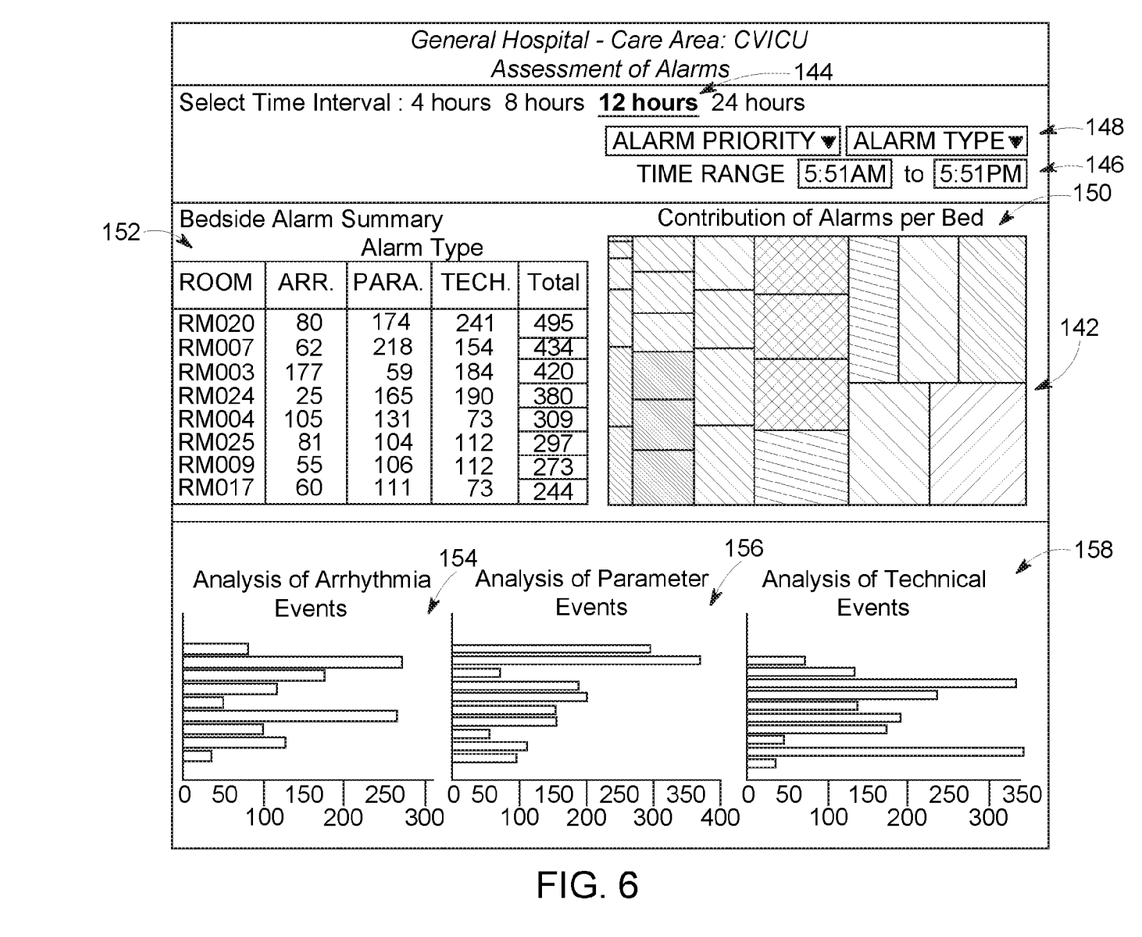
FIG. 6 depicts another exemplary embodiment of an alarm burden dashboard graphical user interface.

In another embodiment, as noted above, the system may be communicatively connected to personnel management unit 34. From the personnel management unit, the system may receive clinician scheduling data which may identify a time definition of shifts of clinicians providing care, or a schedule identifying which clinicians were assigned to provide care to which patients at what time. From this information, the user may further select a filter 148 that filters the alarm data to a particular shift or to view the alarm data associated with a particular clinician.

In the GUI 142 a heat tree map 150 visually presents a summary of the numbers of the alarms produced by each monitoring device and/or room in the monitor care unit. In the heat tree map 15, the number of alarm per patient or device is represented visually by both a color and a size of an icon. In the embodiment depicted in FIG. 6, the total area of the heat tree map 150 represents the total number of current (e.g. within the selected time period) alarms in the care unit. Each icon in the heat tree map indicates a particular room, bed, or device. In an exemplary embodiment in which each patient has an individual room and is monitored by a single patient monitoring device, the concepts of room, bed, patient, and device may all be coextensive. However, in other exemplary embodiments, multiple patients may be assigned to a single room or the system may be monitoring a plurality of medical devices associated with each patient for alarms and alarm management. In other instances, these concepts may result in different values when providing the summary of alarms in the care unit.

In either event, the heat tree map 150 presents the contribution of the alarm burden associated with each patient or each medical device to the current total alarm burden in care unit. This is represented by the size or area of the icon in the heat tree map 150. Additionally, a color of each icon visually presents further summary information regarding the contribution of each patient/room/device to the overall current alarm burden. In a non-limiting example, the color of the individual icon may represent a particular bin or grouping based upon the total number of alarms contributed. These bins may be defined as predetermined values, for example, bins representing values of 10, 50, or 100 alarms. In other embodiments, the value threshold may be relative thresholds, indicating e.g. quartiles or quintiles of the total numbers of alarm or the numbers of rooms/patients/devices broken out into these groups. In a still further exemplary embodiment, different colors or categories may be used to represent standard deviation or other statistical measures from a median or mean number of alarms. In an embodiment, this enables the visual presentation of both the individual contribution of a particular patient/room/medical device to the current total alarm burden, but also provides additional relational context to the individual contribution.

Table 152 provides the individual patient/room/device current alarm totals and also exemplarily breaks down the total number of current alarms by alarm type (e.g. arrhythmia alarms, parameter alarms, and technical alarms).

In the lower portion of the GUI 142 an arrhythmia event summary graph 154, a parameter event summary graph 156, and a technical event summary graph 158 visually present summaries of the alarm events attributed to specific alarms in each of the exemplary three categories of alarm types in the current alarms data from the care unit. By reporting the frequency of events of each of the individual alarms in the different types of alarms, a reviewing clinician can see the relative contribution of specific alarms to the alarm burden in the monitored care unit. As can be seen in these graphs, the outsize contributors to the alarm burden within the care unit are readily apparent with this visual presentation. As a non-limiting example, the events of tachycardia and bradycardia contribute the largest portions of the events in the arrhythmia events graphs 154. Low $S_PO_2$ and high $S_PO_2$ contribute the largest number of events in the parameter events graphs 156. The alarm events of NOIS ECG and ARR suspended contribute the most alarms in the technical events graph 158.

Figure 7:
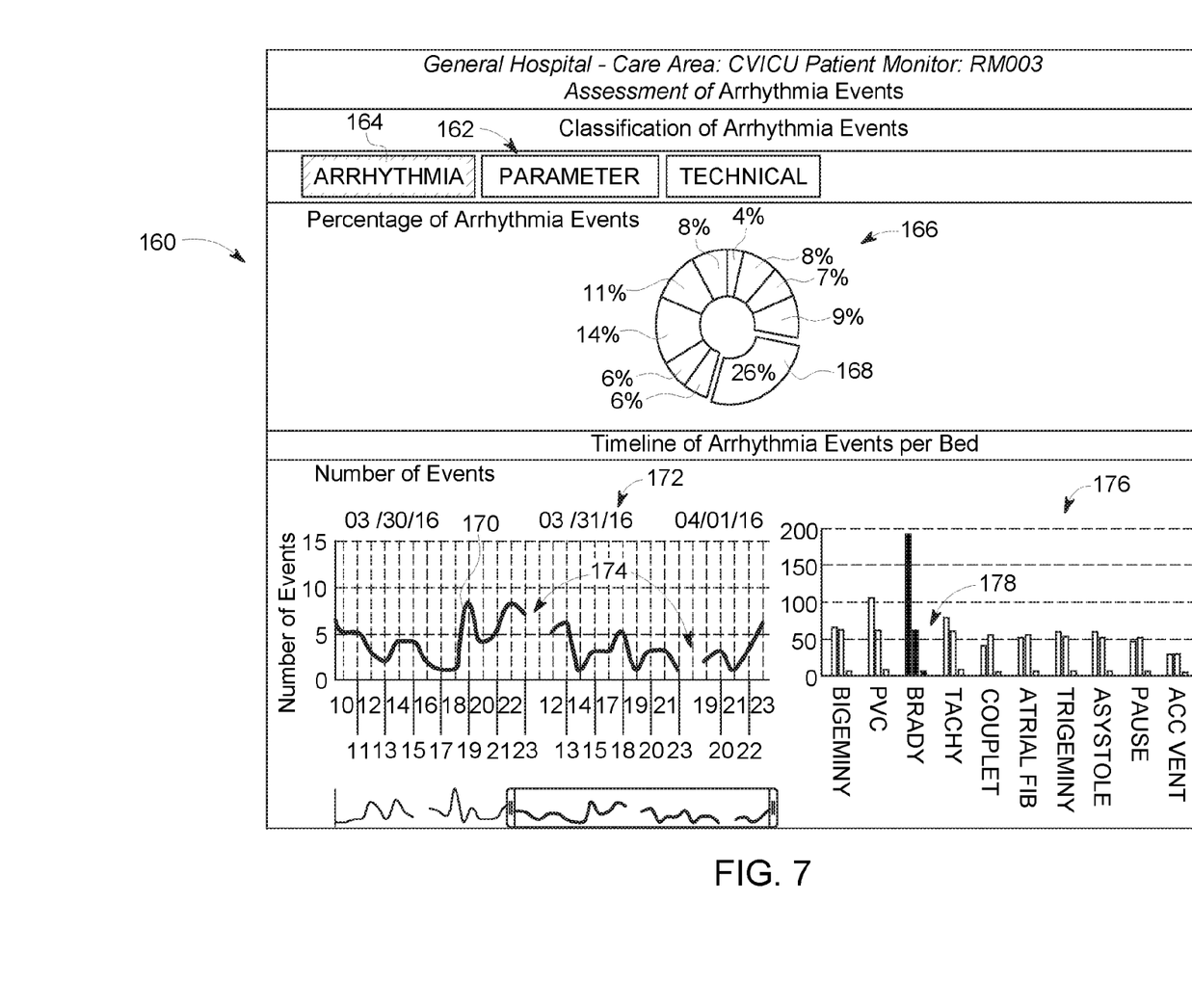
FIG. 7 depicts an exemplary embodiment of an alarm analysis graphical user interface.

In an exemplary embodiment, a user can select any of the patients/rooms/medical devices presented in the GUI 142, for example by selecting any of the icons in the heat tree map 150 or any of the rows of data in the alarm table 152. Selection of one of the patients/room/medical devices will navigate the user to an alarm analysis GUI 160. The alarm analysis GUI 160 as exemplarily depicted in FIG. 7. The alarm analysis GUI 160 further includes navigation buttons 162 for the user to select between arrhythmia alarms events, parameter alarms events, and technical alarm events, in the current alarm data from a particular room, patient, or devices as selected by the user. In FIG. 7, exemplarily, the arrhythmia button 164 has been selected and the GUI 160 visually presents a summary of the current arrhythmia alarm events from the selected patient/room/medical device. For the sake of conciseness and clarity, references herein will be made to the monitoring of alarms associated with a particular patient, while it will recognized that in the same or other embodiments, alarm data related to a particular room and/or medical device may also be used.

An arrhythmia event summary graph 166 visually presents the percentage contribution of each of the arrhythmia along within arrhythmia alarms category is both visually and numerically presented. In the depicted exemplary embodiment, the contribution of each specific alarm to the total number of current alarm events is represented as a percentage as well as a size of an icon 168 in the graph. In another exemplary embodiment, the numerical representation may be a total number of alarm events for each particular alarm.

In an exemplary embodiment, the bradycardia icon 168 in the arrhythmia event summary graph 166 is selected by the user and the system presents the bradycardia alarm data 170 from the selected patient in an alarm event history graph 172. The alarm event history graph 172 plots the number of alarm events, or a rate of alarm events per hour for the bradycardia alarm for a particular patient over a number of days. In an exemplary embodiment, the alarm event history graph 172 includes discontinuities 174 in the alarm data 170. The discontinuities 174 may indicate either times in which the patient was removed from the monitored care unit (e.g. for other intervention or care or in the vent wherein the alarm data is from a particular monitored room and/or medical device, discontinuities 174 in the alarm data 170 may be used to indicate the time period between the room/medical device are used for new patients). Such indications can provide insight to clinicians in identifying particular patients which are more prone to particular types of alarms as well as to see comparative changes in numbers of alarm events to recent historical alarm data. In an exemplary embodiment, when a new patient is monitored, alarm parameter settings may be returned to default settings and indication of a new patient may prompt a clinician to review and/or modify alarm settings for that patient.

Additionally, an alarm response graph 176 visually presents both the frequency of particular alarm events in the current alarm data for the selected patient, but also temporal data broken out and reported by the specific alarms. The temporal data 178 exemplarily includes a maximum duration of an alarm event as well as an average duration of an alarm event. In other embodiments, this may be a clinician response time. Clinician non-responsiveness to alarms can be a sign to symptom of alarm burden and alarm fatigue. Furthermore, alarm duration can be a both significant clinical concern to ensure that clinicians are properly responding to alarms of patient need, while also short alarm duration can often indicate that such alarm events are less severe or further provide an indication that the alarm event was a false positive or did not carry a strong correlation to current patient condition e.g. a momentary patient movement may create a spike in patient heart rate or blood pressure, but if these measurements return to a normal level or a level normal for that patient shortly thereafter, there is no contrary indication even if such spike momentarily produces an alarm event.

It will be recognized that while the GUI 160 exemplarily depicts and has been described in relation to arrhythmia alarm events, similar GUI presentations as the arrhythmia event analysis 56 may be available for parameter event analysis 58 and technical event analysis 60 as referenced in FIG. 2 through the systems and methods as disclosed herein.

As exemplarily depicted in FIG. 2, from the parameter event analysis 58, specific parameters may be further evaluated in the manners as disclosed herein through the use of parameter specific analysis, exemplarily an $S_pO_2$ parameter analysis 62 and a heart rate parameter analysis 64. A heart rate parameter analysis GUI 180 is exemplarily depicted in FIG. 8. The heart rate parameter analysis GUI 180 exemplarily includes a histogram portion 182 and an analysis portion 184. As previously mentioned, embodiments of the system receive physiological data in addition to alarm data from each of the monitored medical devices. The histogram 182 visually presents the received physiological data that is associated with the particular selected alarm, in this case heart rate data.

Figure 8:
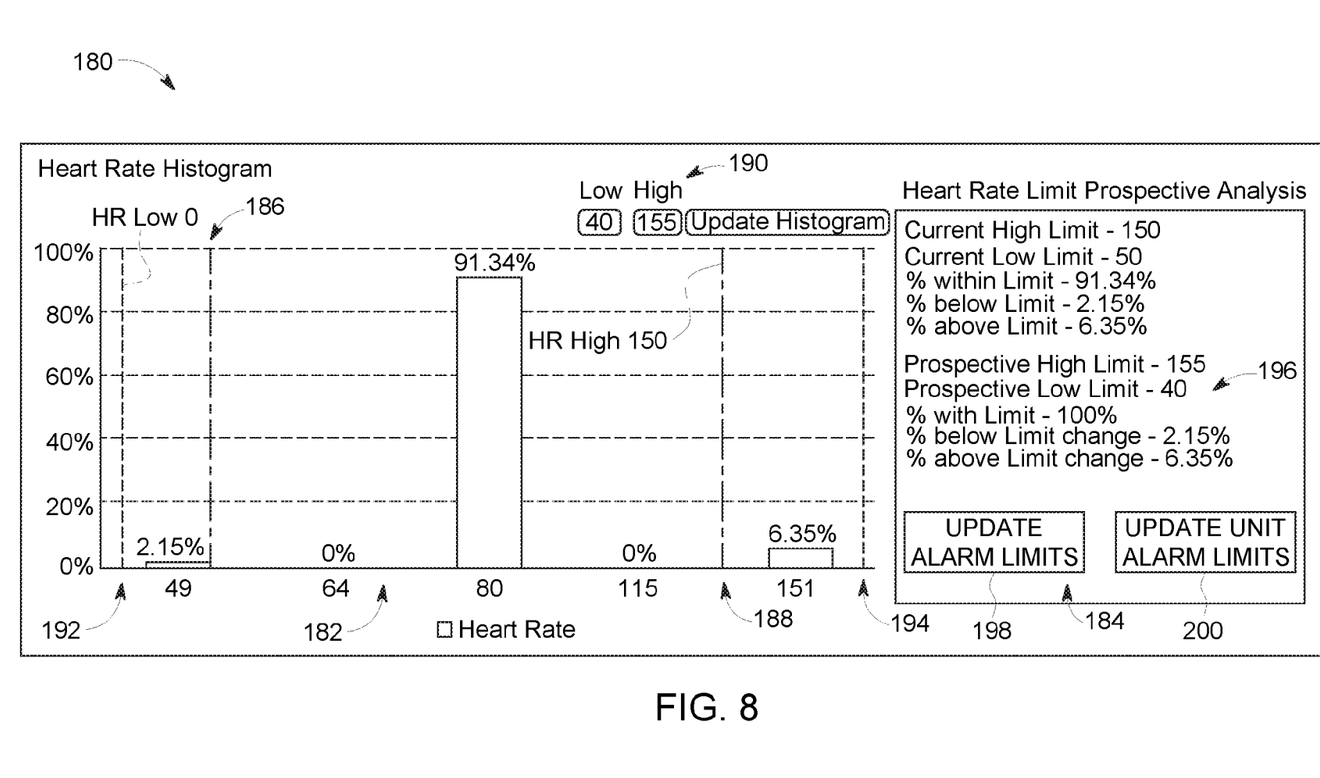
FIG. 8 depicts an exemplary embodiment of an alarm limit analysis graphical user interface.

In an exemplary embodiment, two alarms are associated with the heart rate physiological data. Specifically, a low heart rate limit 186 and a high heart rate limit 188. The current heart rate alarm limit values associated with these alarms are visually presented on the histogram 182 in relation to the histogram relating the associated physiological data of the patient for the particular parameter alarm (heart rate) being considered. The user is able to use this GUI 180 to test prospective new limits for the parameter alarms by entering new threshold values in the user interface 190. By selecting the update histogram button the user interface 190, the histogram 182 can update to graphically depict the prospective low heart rate alarm value 192 which is exemplarily 40 beats per minute and to reflect the proposed high heart rate alarm value 194 which exemplarily is proposed to be adjusted to 155 beats per minute. By making such an adjustment, the prospective analysis portion 184 is updated in a prospective reporting section 196 to indicate the proposed new alarm limit values. The system further determines the effects of such an alarm limit value change and reports an updated percentage of the current physiological parameter values that would fall within the newly proposed alarm limits, while reporting a percentage change in the alarms that would still fall below the proposed lower limit 192 or above the proposed upper limit 194, thus resulting in an associated parameter alarm. In another embodiment, the system may report a total number of alarm events which would fall into each category rather than a percentage falling above, below, and within the alarm threshold limits.

These tools, as explained in further detail herein, enable a user to evaluate the effect that various alarms limit changes would have on the number of alarms produced while monitoring a particular patient. Some patients may exemplarily have higher or lower baseline physiological values and while a particular parameter value may be outside of a normal range for the general population, may pose less of a risk to a particular individual patient. Therefore, a user of embodiments of the system and methods as described herein can prospectively evaluate various alarm value setting changes before deciding upon new alarm limit values. After the user has decided upon new alarm limit values, the user may select and update alarm limits button 198 to send a communication from the system back to a medical device to update the alarm limits of the medical device which is currently being reviewed by the clinician. If the clinician desires to update the alarm limit for all of the medical devices in a particular care unit, the user can alternatively select the update unit alarm limits button 200 to update the alarm limit settings of multiple medical devices at one time.

In another embodiment, after an analysis of alarm limits described above, the system may instead send a notice of a recommended It will be recognized that in other embodiments, the system may be provided with other forms of medical device data as is evaluated in the application other alarms, for example, arrhythmia alarms or technical alarms. Thus, similar graphical user interfaces as described above may also be made available for evaluation and adjustment of alarm limit parameters with respect to arrhythmia and/or technical alarms as well.

Figure 9:
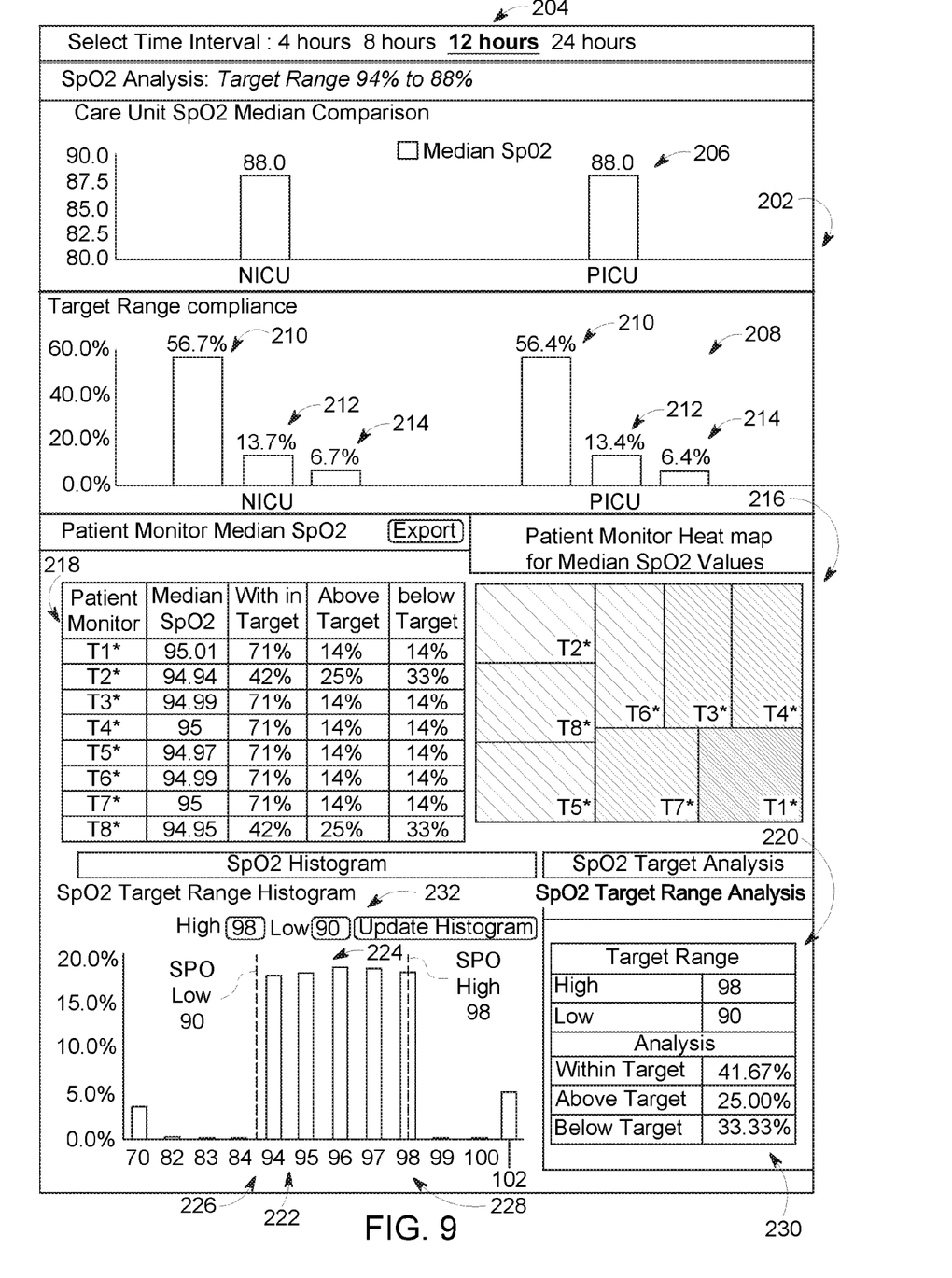
FIG. 9 depicts another exemplary embodiment of an alarm limit analysis graphical user interface.

Referring back to FIG. 2 in still further exemplary embodiments, a user may navigate to a parameter limit assessment 68. An exemplary embodiment of a parameter limit assessment GUI 202 is depicted in FIG. 9. The exemplary embodiment of the parameter limit assessment GUI 202 exemplarily extends the analysis from the previous alarm parameter analysis GUI 180 to comparisons between the alarm parameters set between multiple care units. The GUI 202 exemplarily enables the user to select a time interval for the current physiological data and alarm data to be analyzed at 204. In a physiological data graph 206 a summary of the current physiological data from the selected care units is presented. In exemplary embodiments, this may be presented as a median value (as depicted in the graphs 206 of FIG. 9) or may be a mean value or another statistical or other summary representation of the current physiological data. A compliance graph 208 provides a visual representation of the percentage of physiological data in each of the monitored care units (e.g. NICU and PICU) that exemplarily falls within the current alarm limit target range 210, fall above the target range 212, or fall below the target range 241. This exemplarily provides the user with contact regarding the frequency with which alarm events occur relative to the total physiological data measurements.

In embodiments, the same information may be presented on a individualized basis in an individual compliance heat tree map 216. Similar to the heat tree map previously described above, the individual compliance heat tree map 216 exemplarily visually presents the compliance data for each of the individual monitored patients. In an exemplary embodiment, each icon on the heat tree map 216 represents an individual patient. The size of each of the icons exemplarily represents the total number of alarm events for being out of target range or similarly reporting the percent of the physiological data received outside of the target range. In an exemplary embodiment, the color of each icon represents the median $S_PO_2$ value for each individual patient. In a still further exemplary embodiment, the color of the icons may represent an absolute deviation from the median or mean physiological parameter value for a particular care unit or across all of the monitored care units. A table 218 exemplarily presents the associated numerical value for the median $S_PO_2$ value for each of the patients.

Similar to the alarm parameter analysis GUI 180 as described above, a similar alarm analysis GUI 220 can be presented as a part of the GUI 202. Such a GUI 220 exemplarily may work in a similar manner to that as described above. Specifically, a histogram 220 presents both the physiological data resulting in the determination of alarm events 224 as well as a graphical presentation of the low alarm limit 226 and the high alarm limit 228. The target analysis portion 230 reports the target range compliance associated with the selected low alarm limit 226 and high alarm limit 228 in view of the received current physiological data 224. In embodiments, the clinician may use this information to generally evaluate alarm compliance and alarm limit setting across two or more care units. After such analysis, a user may navigate to one of the previously disclosed alarm limit analysis GUIs for evaluation and selection of new alarm limits. In an additional embodiment, the target analysis portion 230 may similarly include a report on determined compliance with prospective alarm limit values which may be entered through user interface 232 to update the histogram in such an exemplary embodiment, upon deciding upon updated alarm limit values, the user may make an input and/or selection to extend such updated limited values to the medical devices of the monitored care unit.

Figure 3:
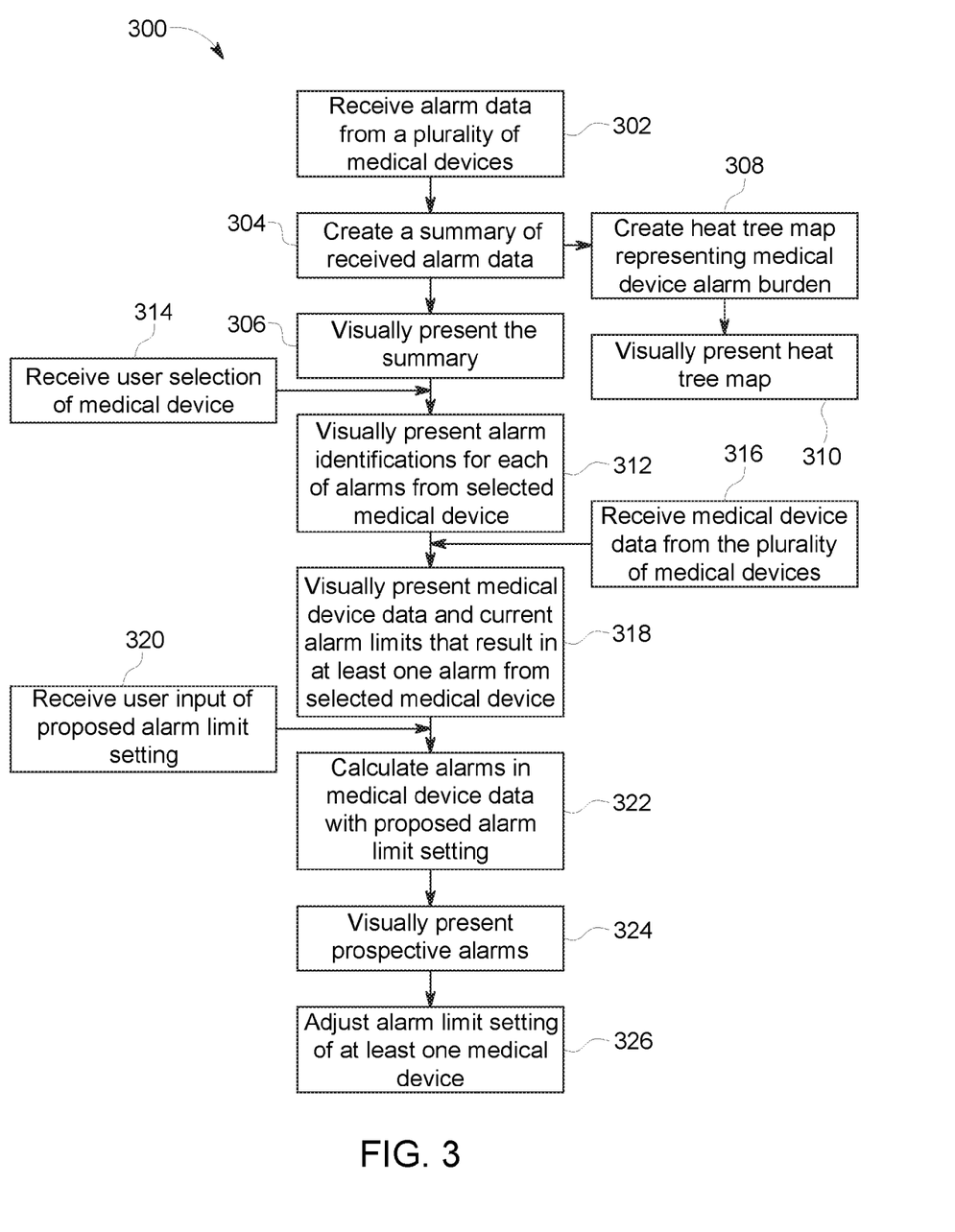
FIG. 3 is a flow chart that depicts an exemplary embodiment of a method of medical device alarm management.

FIG. 3 is a flow chart that depicts an exemplary embodiment of a method 300 of medical device alarm management. The method 300 begins at 302 where alarm data from a plurality of medical devices is received. The plurality of medical devices may each be associated with a different patient or multiple medical devices may be associated with a single patient. Patients may exemplarily be located in a particular care unit of a hospital or across multiple care units of a hospital and still further exemplary embodiment the medical devices may be located in a plurality of care units. The alarm data may exemplarily have indications of alarm events from alarms of a plurality of alarm types. Such alarm types may include, but are not limited to arrhythmia alarms, parameter alarms, and technical alarms. In exemplary embodiments, such alarm events are detected by algorithmically comparing medical device data to alarm definitions which may use value, logic, or other algorithms to define alarm event conditions. The medical device data may include machine data from the medical devices themselves as well as physiological data from the patient, including, but not limited to directly measured physiological parameters, as well as physiological signals for example electrocardiogram signals or physiological parameters resulting from analysis thereof. The alarm data may further include information regarding alarm duration, or if an alarm is locally silenced by a clinician.

In an embodiment, machine data is collected internally from the medical device itself. Machine data can include alarms, device status, settings, messages, and measured operational data. Machine data may further includes settings and values that represent specific actions taken with the medical device for example, in response to automated controls or due to clinician inputs. For example, in an anesthesia delivery machine, this may include changes to oxygen and/or anesthetic agent concentrations. The machine data may further include clinical and/or technical alarms initiated by the medical device or device diagnostic information. In other examples, machine data may include flow sensors or valve cycles, processor clock speeds, component voltages. Still further examples of the machine data include proactive or predictive service alerts from the medical device, maintenance checkout information and/or processor clock cycle signals or power signals or other operational signals from various components of the medical device indicative that the medical device is turned on, in use, in operation, held in a stand by condition, or turned off.

At 304 a summary of the received alarm data is created. The summary is created from the alarm data received from the plurality of medical devices exemplarily by determining an alarm identification of each of the alarms of the plurality of alarms and a frequency of occurrence of each alarm identification in the plurality of alarms. This summary is visually presented at 306. In exemplary embodiments, the visual presentation occurs in a graphical user interface presented on a graphical display and may include one or more of a pie chart, bar graphs, and/or tables to either or both visually present the summary graphically and numerically.

In an exemplary embodiment, the summary of received alarm data from 304 may be further used to determine an alarm burden created by each of the plural of medical devices. In an exemplary embodiment, the summary of received alarm data is used at 308 to create a heat tree map which represents medical device alarm burden. The heat tree map, as described above, may exemplarily visually present the alarm burden of various medical devices relative to both a color and a size of icons in the heat tree map. The heat tree map is visually presented exemplarily in the GUI presented on the graphical display.

In further exemplary embodiments, the summary of received alarm data may further be created in view of a user input of a selection of a time period for consideration. The time period may, in one exemplary embodiment be an identification of a historical time range, while in another exemplary embodiment, the time period may exemplarily be a time period to be considered to current alarm data. The current alarm data may extend up to a most recent update of alarm information, which may exemplarily include real time updates of alarm data and the time period may exemplarily extend one hour, two hours, four hours, twelve hours, or another length of time as may be recognized by a person of ordinary skill in the art.

At 312, alarm identifications for alarms identified in the alarm data are visually presented. In one exemplary embodiment, the alarm identifications may be for all of the alarm identifications of the plurality of medical devices, while in another embodiment, the visually presented alarm identifications may be limited to only those alarm identifications of medical devices within a selected care unit. In a still further exemplary embodiment, the system at 314 receives a user selection of a specific medical device and the visual presentation of the alarm identifications include a visual presentation of each of the alarms identified in the alarm data for the selected medical device. At 316 medical device data is received from each of the plurality of medical devices from which alarm data is received. It will be recognized that in exemplary embodiments, the medical device data includes machine data and/or physiological data from the medial devices which is evaluated to result in the initiation of alarm events represented in the alarm data.

At 318 the medical device data is visually presented. Exemplarily, the medical device data that results in at least one of the alarms in the alarm data is visually presented. In an exemplary embodiment, the medical device data is presented in a histogram of medical device data, exemplarily showing the values and frequencies of particular medical device data values in a particular selected time period of medical device data and alarm data. In a still further exemplary embodiment, the medical device data is visually presented along with a visual presentation of the current alarm limits that result in at least one alarm from the selected medical device. This is exemplarily depicted in the alarm parameter analysis GUI 180 depicted in FIG. 8.

At 320, the system receives a user input of a proposed alarm limit setting. Exemplarily, this input is provided through the user input 190 in the GUI 180 depicted in FIG. 8. The received user input of a proposed alarm limit setting is used at 322 to calculate alarm events in the medical device data that would have occurred with the proposed alarm limited setting. These calculated prospective alarms are visually presented at 324. In an exemplary embodiment, this visual presentation of the prospective alarm may exemplarily be a numerical or percentage of prospective alarms under the proposed alarm limit settings. This is exemplarily depicted in the prospective analysis portion 184 of the GUI 180 in FIG. 8. In a still further exemplary embodiment, the visual presentation may further include a percentage change in the number of alarms and the changes as they pertain to specific alarm limits changed in the prospective alarm limits.

Upon the user being satisfied with the proposed alarm limit settings, upon a user input at 326, the alarm limit settings of at least one medical device are adjusted exemplarily by sending the post alarm limit settings to one or more of the medical devices from the medical device alarm management system. In one embodiment, the alarm settings of a single medical device are adjusted, while in another embodiment, the proposed alarm limit settings are adjusted for all of the same medical device in a care unit of hospital facility.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for medical device alarm management, the system comprising:
   a plurality of medical devices that produce medical device data and generate a plurality of alarms based upon analysis of the medical device data;
   a processor that receives alarm data identifying each of the plurality of alarms from each of the plurality of medical devices, the processor receives the medical device data from the plurality of medical devices and categorizes each of the plurality of alarms in the alarm data into a plurality of alarm types based upon the alarm data, and aggregates the alarm data to a total number of alarms, the processor calculates a device contribution to the plurality of alarms by each device of the plurality of medical devices;
   a graphical display operable by the processor to visually present a summary of the plurality of alarms identified in the received alarm data, the summary comprising the total number of alarms, the device contribution to the plurality of alarms by each device, and an alarm type from the plurality of alarm types for each of the plurality of alarms; and
   a user input device communicatively connected to the processor and operable to receive at least one user input of a selection of a medical device of the plurality of medical devices wherein upon receiving the selection of the medical device, the processor operates the graphical display to visually present an identification of each of the alarms from the selected medical device and a frequency of each alarm identification of the plurality of alarms from the selected medical device.

2. The system of claim 1, wherein the medical device data comprises at least one of patient physiological data and device technical data.

3. The system of claim 1, wherein the plurality of medical devices are located across a plurality of locations.

4. The method of claim 3, wherein the processor aggregates alarm totals from the medical devices at each location of the plurality of locations and operates the graphical display to visually present alarm totals for each of the plurality of locations.

5. The system of claim 1, wherein the processor receives the alarm data in real time and updates the visual presentation of the total of the plurality of alarms and the visual presentation of the identification of each of the alarms in real time to reflect the received alarm data.

6. The system of claim 1, further comprising:
   wherein the processor operates the graphical display to visually present at least one alarm threshold setting that defines at least one alarm and to visually present the medical device data associated with the at least one alarm;
   wherein upon receiving an adjustment to the at least one alarm threshold setting with the user input device, the processor operates the graphical display to visually present the adjustment to the at least one alarm threshold setting; and wherein the processor calculates a retrospective number of alarm events based upon the medical device data and the adjustment to the at least one alarm threshold setting.

7. The system of claim 6, wherein upon receiving an input at the user input device to accept the adjustment to at least one alarm threshold setting, the processor electronically communicates the adjustment to at least one alarm threshold setting to at least one medical device of the plurality of medical devices to adjust at least one alarm threshold setting of the at least one medical device.

8. The system of claim 1, further comprising:
wherein the processor operates the graphical display to visually present a lower threshold limit and an upper threshold limit that define at least one alarm and to visually present the medical device data associated with the at least one alarm;
wherein upon receiving an adjustment to at least one of the lower threshold limit and the upper threshold limit, the processor operates the graphical display to visually present the adjustment; and
wherein the processor calculates percentages of the medical device data below the lower threshold limit, above the upper threshold limit, and within the lower threshold limit and upper threshold limit, after the adjustment.

9. The system of claim 8, wherein the processor electronically provides an adjustment recommendation to a user associated with at least one medical device of the plurality of medical devices.

10. A method of medical device alarm management, the method comprising:
receiving alarm data from a plurality of medical devices, the alarm data comprising a plurality of alarms from the plurality of medical devices;
aggregating a total alarm burden from the total number of alarms from each of the plurality of medical devices;
calculating a contribution by each medical device to the total alarm burden;
creating a summary of the received alarm data from the plurality of medical devices by determining an alarm identification of each alarm of the plurality of alarms and frequency of each alarm identification in the plurality of alarms;
visually presenting the calculated contribution by each medical device to the total alarm burden;
visually presenting the summary of alarms received from the plurality of medical devices; and
upon receiving a selection of a medical device of the plurality of medical devices, visually presenting the alarm identifications of each of the alarms from the selected medical device and the frequency of each alarm identification of the plurality of alarms from the selected medical device.

11. The method of claim 10, further comprising receiving a selection of a time period for consideration and determining an alarm burden created by each of the plurality of medical devices.

12. The method of claim 11, further comprising:
calculating a contribution from each alarm identification to the total alarm burden;
visually presenting the contribution from each alarm identification to the total alarm burden.

13. The method of claim 10, further comprising:
receiving medical device data from the plurality of medical devices; and
visually presenting the medical device data resulting in at least one alarm of the plurality of alarms in the alarm data.

14. The method of claim 13, herein medical device data is visually presented in a histogram of medical device data.

15. The method of claim 14, further comprising visually presenting current alarm threshold settings in connection with medical device data.

16. The method of claim 15, further comprising:
receiving an adjustment to at least one alarm threshold setting;
visually presenting the adjustment to the at least one alarm threshold setting; and
calculating and visually presenting a number of alarm events based upon the medical device data with the adjustment to at least one alarm threshold setting.

17. The method of claim 16, further comprising upon receiving a user input to accept the adjustment to at least one alarm threshold setting, electronically communicating the adjustment to at least one alarm threshold setting to at least one medical device of the plurality of medical devices to adjust at least one alarm threshold setting of the at least one medical device.

18. The method of claim 16, wherein the medical device data is physiological data, and the alarm events are physiological parameter alarm events.

19. The method of claim 12, wherein the visual presentation comprises a heat tree map representing a number of alarms from each medical device as a size of a graphical icon and an assessment of the number of alarms from each medical device as a color of the graphical icon.

20. The method of claim 10, further comprising:
presenting a first visual presentation of historical alarm data from a plurality of medical devices wherein a clinician uses the first visual presentation of historical alarm data to select a filtering criteria for the plurality of alarms for alarm burden reduction;
presenting a second visual presentation of historical alarm data temporally apart from the presentation of the first visual presentation of historical alarm data; and
evaluating alarm burden reduction by comparing the first visual presentation of historical alarm data to the second visual presentation of historical alarm data.

21. A method of medical device alarm management, the method comprising:
receiving alarm data from a plurality of medical devices, the alarm data comprising a plurality of alarms from the plurality of medical devices;
receiving medical device data from the plurality of medical devices, the medical device data having been processed by a respective medical device of the plurality of medical devices using at least one alarm parameter to initiate the plurality of alarms in the alarm data;
visually presenting a summary of alarms received in the alarm data from the plurality of medical devices;
aggregating a total alarm burden from a total number of alarms from each of the plurality of medical devices;
calculating each medical device's contribution to the total alarm burden;
visually presenting each medical device's contribution to the total alarm burden; and
upon receiving a selection of a medical device of the plurality of medical devices, visually presenting an identification of each of the alarms from the selected medical device and a frequency of each alarm identification of the plurality of alarms from the selected medical device.

22. The method of medical device alarm management of claim 21, further comprising:

upon receiving a selection of an identified alarm from the selected medical device, visually presenting medical device data from the selected medical device associated with the identified alarm and visually presenting at least one alarm parameter associated with the identified alarm.

* * * * *